(12) United States Patent
Yamamoto et al.

(10) Patent No.: US 8,318,799 B2
(45) Date of Patent: *Nov. 27, 2012

(54) THERAPEUTIC AGENT FOR SUBSTANCE DEPENDENCE

(75) Inventors: Tsuneyuki Yamamoto, Fukuoka (JP); Fumio Yoneda, Matsubara (JP); Kazuhiko Morimoto, Matsubara (JP)

(73) Assignees: National University Corporation Kyushu University, Fukuoka (JP); Fujimoto Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/851,091

(22) Filed: Aug. 5, 2010

(65) Prior Publication Data
US 2010/0298426 A1 Nov. 25, 2010

Related U.S. Application Data

(62) Division of application No. 11/791,116, filed as application No. PCT/JP2005/021344 on Nov. 21, 2005, now Pat. No. 7,825,158.

(30) Foreign Application Priority Data

Nov. 25, 2004 (JP) ................................. 2004-339996

(51) Int. Cl.
*A61K 31/343* (2006.01)
*A61P 25/30* (2006.01)
(52) U.S. Cl. ........................................ 514/468; 514/469
(58) Field of Classification Search .................. 514/468, 514/469
See application file for complete search history.

(56) References Cited

U.S. PATENT DOCUMENTS
6,391,914 B1    5/2002   Knoll et al.

FOREIGN PATENT DOCUMENTS
JP    2003089643    *  3/2003
WO    01/77074        10/2001

OTHER PUBLICATIONS

Shimazu et al., "Pharmacological Studies with Endogenous Enhancer Substances: β-Phenylethylamine, Tryptamine, and their Synthetic Derivatives," Progress in Neuro-Psychopharmacology & Biological Psychiatry, vol. 28, No. 3, pp. 421-427 (2004).
Bartzokis et al., "Selegiline Effects on Cocaine-Induced Changes in Medial Temporal Lobe Metabolism and Subjective Ratings of Euphoria," Neuropsychopharmacology, vol. 20, No. 6, pp. 582-590 (1999).
International Search Report dated Dec. 27, 2005 in International Application No. PCT/JP2005/021344.

* cited by examiner

*Primary Examiner* — Sreeni Padmanabhan
*Assistant Examiner* — Sahar Javanmard
(74) *Attorney, Agent, or Firm* — Wenderoth, Lind & Ponack, L.L.P.

(57) ABSTRACT

The present invention provides a therapeutic agent for substance dependence, which prevents relapse/recurrence of compulsive substance-taking behavior based on craving for addictive substances such as stimulant substances, opioids, barbiturate type anesthetics, hallucinogens, cocaine, hemp, cannabis, alcohol, or volatile organic solvents. (−)-1-(Benzofuran-2-yl)-2-propylaminopentane or a pharmacologically acceptable acid addition salt thereof is useful as a therapeutic agent for substance dependence, which prevents relapse/recurrence of compulsive substance-taking behavior associated with craving for addictive substances.

4 Claims, 7 Drawing Sheets

THERAPEUTIC AGENT FOR SUBSTANCE DEPENDENCE

This application is a Divisional of application Ser. No. 11/791,116, filed May 21, 2007 now U.S. Pat. No. 7,825,158, which is the National Stage of International Application No. PCT/JP2005/021344, filed Nov. 21, 2005.

TECHNICAL FIELD

The present invention relates to a therapeutic agent for substance dependence, which comprises (−)-1-(benzofuran-2-yl)-2-propylaminopentane or a pharmaceutically acceptable acid addition salt thereof as an active ingredient.

BACKGROUND ART

Substance dependence as defined by the WHO is "A state, psychic and sometimes also physical, resulting from the interaction between a living organism and a drug, characterized by behavioural and other responses that always include a compulsion to take the drug on a continuous or periodic basis in order to experience its psychic effects, and sometimes to avoid the discomfort of its absence.". That is, substance dependence can be divided into psychic dependence and physical dependence. In psychic dependence, there appears a strong desire "craving" for taking a certain substance, and in physical dependence, withdrawal symptoms appear upon interruption of dosing. A dependence-producing substance may also produce tolerance in those who take it, thus causing an increase in intake thereof. In the withdrawal syndrome, craving for a large amount of a substance is brought about due to extreme suffering, thus falling in a vicious cycle to make impossible to keep away from the substance. This vicious cycle constitutes substance dependence.

Substances causing substance dependence include stimulants (amphetamine, methamphetamine, MDMA), opioids (morphine, heroin), barbiturate type anesthetics, hallucinogens (LSD), cocaine, hemp (marijuana), cannabis, benzodiazepine type compounds (sedatives, hypnotics, anxiolytics), alcohol, and volatile organic solvents. Some stimulant substances have an appetite-suppressing effect and are thus used sometimes for dieting. It is also noted that some stimulant substances are mixed in "diet pills". These drugs are those regarded as most important for measures against drug abuse in Japan because of the hazardous nature and prevalence thereof. Various problems with substance dependence are not only medical problems but also serious social problems.

If drug abuse is repeated, psychopathic symptom is increasingly experienced as chronic effect. Frequently found symptom examples include hyperacusia by which ambient sounds are heard louder than actual sounds and auditory hallucinations by which voices are heard in one's head, together with the noise of an air conditioner and the sound of running water, or voices coming from nowhere are heard without relation to such noise or sound. Such voices may be voices of his family, friends, acquaintances in some cases or completely unfamiliar voices in other cases and are heard to be accusatory, threatening, mandatory or interfering. If his life or inner thoughts are guessed rightly by the voices, he believes that a device such as a bugging device has been set somewhere, and will seek for it under the roof or floor or will disassemble electrical utility equipments. Inextricably linked to such false feeling, he comes to have a suspicion of being soiled by someone and harbors suspicion against his family and friends or becomes paranoid. Everywhere he goes, he has the idea of being chased by a person (for example, a policeman, a mafia member etc.) or has a visual hallucination that he saw that person lurking in the shadows. Such hallucinations and delusions resemble those of schizophrenia. There are also cases where the subtleties of emotion, or willingness, are attenuated through drug abuse for a prolonged period, and hallucinations and delusions in such cases may be hardly discriminated from those of schizophrenia.

The problem of psychopathic symptom caused by substance abuse lies in long-term persistence after chronic abuse, and in relapse due to alcohol drinking, sleeplessness, extreme stress etc. The former is called sequelae of substance abuse and the latter is called flashback phenomenon. Such pathology lasting long even after abstinence from substance use are obstacles for people who wish to recover from substance dependence, and this is another fear of substance abuse.

Therapy of substance dependence at present is initiated by abstaining from its causative substance, and substance therapy has been regarded as having little effect. If a sleeping pill or tranquilizer is administered without careful consideration, abuse of, or dependence on, such a prescription drugs may be caused, and in fact it is said that there are many patients with abuse of prescription drugs in addition to stimulant abuse.

As prior arts relating to therapeutic agents for substance dependence, Patent Document 1 discloses azabicyclo derivatives or benzoic acid derivatives (5-HT antagonist); Patent Document 2 discloses rolipram (phosphodiesterase inhibitor); Patent Document 3 discloses ifenprodil; Patent Document 4 discloses an inhibitor of degradation of an endogenous neuropeptidyl opioid; and Japanese Patent 5 discloses prophylaxis/therapy of substance dependence caused by dopamine autoreceptor agonists etc., as well as alleviation/prophylaxis of withdrawal syndrome. However, any of these therapeutic agents for substance dependence cannot be said to be satisfactory in their effect and are still not put to practical use.

Patent Document 1: Japanese Patent No. 2765845
Patent Document 2: JP-A1-HO 9-221423
Patent Document 3: JP-A1-H 11-29476
Patent Document 4: Pamphlet of International Publication WO89/03211
Patent Document 5: Western Germany Patent Application (Laid-Open) No. 3930282

DISCLOSURE OF THE INVENTION

Problems to be Solved by the Invention

Accordingly, the inventors sought the mechanism of relapse/recurrence of craving for substance using a behavioral pharmacological and biochemical approach, that is, they made an intensive study using a drug self-administration procedure in order to develop therapeutic agents for substance dependence as well as to elucidate the mechanism of relapse/recurrence.

The drug self-administration procedure as referred to herein is outlined as follows:

First, an experimental animal is allowed to learn the drug self-administration behavior of pressing a lever to attain a substance. The animal is given a substance-containing solution simultaneously with a light-tone stimulus. After the animal is allowed to learn the substance self-administration behavior, the substance-containing solution is replaced by physiological saline. The behavior of eagerly pressing the lever for acquiring the substance comes to be observed in the experimental animal having learned the substance self-administration behavior. This behavior is regarded as substance-seeking behavior. This substance-seeking behavior is gradually decreased by repeated infusion of physiological saline and is eventually extinguished. However, the substance-seeking behavior will recur by the same light-tone stimulus (drug-associated stimuli) used during the self-administration training to the experimental animal or by administrating a substance inducing the central stimulant effect. This experimental system was used to examine the effect of various compounds.

Means for Solving the Problems

The inventors sought the mechanism of relapse/recurrence of craving for substance behavioral pharmacologically and biochemically using this drug self-administration procedure. As a result they found that (−)-1-(benzofuran-2-yl)-2-propylaminopentane known previously as a compound having a psychotropic effect, an antidepressant activity, and an antiparkinsonian effect or anti-Alzheimer disease effect has an excellent effect as a therapeutic agent for substance dependence, and the present invention was thereby completed. That is, the present invention provides:
(1) A therapeutic agent for substance dependence, which comprises (−)-1-(benzofuran-2-yl)-2-propylaminopentane or a pharmaceutically acceptable acid addition salt thereof as an active ingredient;
(2) The therapeutic agent for substance dependence according to the above (1), which suppresses the induction of substance-seeking behavior caused by substance dependence;
(3) The therapeutic agent for substance dependence according to the above (1), wherein the substance dependence is caused by stimulant substances, opioids, barbiturate type anesthetics, hallucinogens, cocaine, hemp, cannabis, alcohol, or volatile organic solvents;
(4) The therapeutic agent for substance dependence according to the above (1), wherein the substance dependence is caused by stimulants;
(5) The therapeutic agent for substance dependence according to the above (2), wherein the substance dependence is caused by stimulants;
(6) A method of treating substance dependence, which comprises administering an effective amount of (−)-1-(benzofuran-2-yl)-2-propylaminopentane to a substance-dependent patient;
(7) A method of suppressing the induction of substance-seeking behavior, which comprises administering an effective amount of (−)-1-(benzofuran-2-yl)-2-propylaminopentane to a substance-dependent patient with substance-seeking behavior; and
(8) Use of (−)-1-(benzofuran-2-yl)-2-propylaminopentane in the manufacture of a medicament for treatment of substance dependence.

The (−)-1-(benzofuran-2-yl)-2-propylaminopentane used in the present invention (also referred to in this specification as "the compound of the present invention") is a known compound having the chemical structure represented by formula I below, and International Publication WO00/26204 describes its psychotropic effect, antidepressant activity, antiparkinsonian effect or anti-Alzheimer disease effect together with its production method and physical properties.

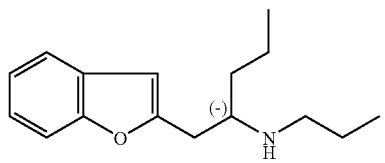

The compound of the present invention has neuroprotective effects attributable to antiapoptotic effect (Life Sciences 72, 2785-2792 (2003)) and improves the reduction in spontaneous motor activity induced by reserpine, suggesting that its effect is mediated by an increase in dopamine release (Eur. J. Pharmacol. 421, 181-189 (2001)). The use of the compound of the present invention as a therapeutic agent for substance dependence has never been reported in any literatures including those mentioned above.

Specific examples of pharmacologically acceptable acid addition salts of (−)-1-(benzofuran-2-yl)-2-propylaminopentane used in the present invention include addition salts of inorganic acids such as hydrochloric acid, sulfuric acid, hydrobromic acid, nitric acid and methanesulfonic acid or organic acids such as gluconic acid, tartaric acid, maleic acid, fumaric acid, succinic acid, malic acid, citric acid and mandelic acid.

The compound used in the present invention and its pharmaceutically acceptable acid addition salt, when used as the pharmaceutical preparation described above, can be mixed usually with a carrier, excipient, diluent, solubilizing agent etc. and safely administered orally or parenterally in the form of tablets, powders, granules, capsules, syrup, injection or the like. Although the dosage can vary depending on a variety of factors such as medical condition, age, sex, weight of the patient, the pharmaceutical preparation can be administered to an adult usually once or several times orally in an amount of about 0.1 mg to 1000 mg, preferably 1 mg to 500 mg, per day. However, when the dose administered once is too high, the substance-seeking behavior may be caused in some cases, and thus an effective and minimum dose is preferably selected.

EFFECT OF THE INVENTION

The substance dependence in the present invention includes that is attributable to abuse of substances or chemical substances such as stimulants (amphetamine, methamphetamine, MDMA), opiods (morphine, heroin), barbiturate type anesthetics, hallucinogens (LSD), cocaine, hemp (marijuana), cannabis, benzodiazepine type compounds (sedatives, hypnotics, anxiolytics), alcohol, and volatile organic solvents.

BEST MODE FOR CARRYING OUT THE INVENTION

Figure 1:
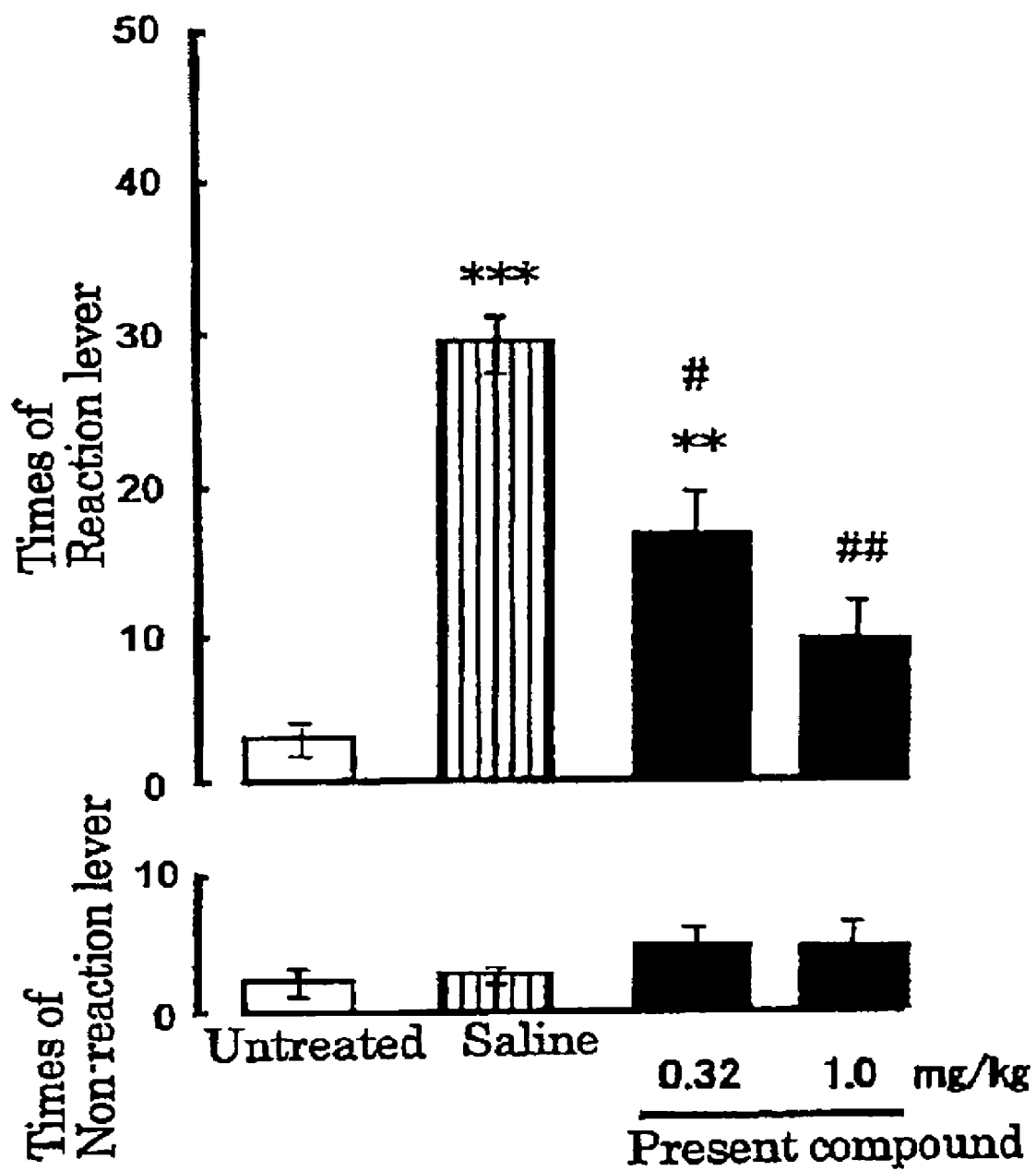
FIG. 1 is a graph showing the inhibitory effect of the compound of the present invention on the substance-seeking behavior by single administration. After single administration of the compound of the present invention (1.0 mg/kg, i.p.), the number of active lever-pressings, indicating the methamphetamine-seeking behavior induced by drug-associated cue, was observed for 30 minutes, and the result is shown in the graph. The symbol * indicates statistical significance vs. a non-treated group at the following levels *: $p<0.005$, : $p<0.01$, *: $p<0.001$. The symbol # indicates statistical significance vs. a physiological saline-treated group at the following levels #: $p<0.05$, ##: $p<0.01$, ###: $p<0.001$. This description of * and # will hereinafter applies.

Hereinafter, the present invention is described in more detail by reference to the Example (Experimental Examples).

EXAMPLE 1

Effects on Addictive Substance-Seeking Behavior

Using methamphetamine as an addictive substance, the following experiments were carried out according to a method described in Neuropsychopharmacology, 29, 1470-1478 (2004).

Preparation of Experimental Animals

A catheter for self-administration of methamphetamine (inner diameter of 0.5 mm, outer diameter of 1.0 mm) was inserted into the right jugular vein of male Wister/ST rats (250 to 350 g), and the end of the catheter was anchored to just outside the right atrium. An operant box used in the experiment was equipped with 2 levers. One is an active lever by which when pressed once (fixed-ratio 1 (FR1)), infusions of a very low dose of methamphetamine (0.02 mg per injection) was paired with onset of a 6-sec tone (70 dB/7 kHz) and light (300 lux) compound stimulus. The other is an inactive lever by which neither the drug-associated cue nor the infusion of methamphetamine are given.

After the animal was allowed to get methamphetamine self-administration behavior (methamphetamine-taking behavior) by the self-administration experiment for 10 days (2 hours per session), physiological saline was substituted for methamphetamine, to carry out an extinction process for 5 days (1 hour per session without drug-associated cue).

The hydrochloride compound of the present invention used in the experiment had a melting point of 165.0 to 166.0° C., an optical purity of 93% ee and specific rotation: $[\alpha]_D^{20}=-4.08$ (c=4.0 methanol).

The number of pressing the 2 levers (the active lever and inactive lever) by the experimental animal was used as an indicator of the substance-seeking behavior.

Experiment 1: The Inhibitory Effect by Single Administration of the Compound of the Present Invention on Substance-Seeking Behavior On day 6 of the extinction process, substance-seeking behavior ("craving") was induced by drug-associated cue (tone and light) or by administering a low dose of methamphetamine (1.0 mg/kg, intraperitoneal (i.p.) administration).

Figure 2:
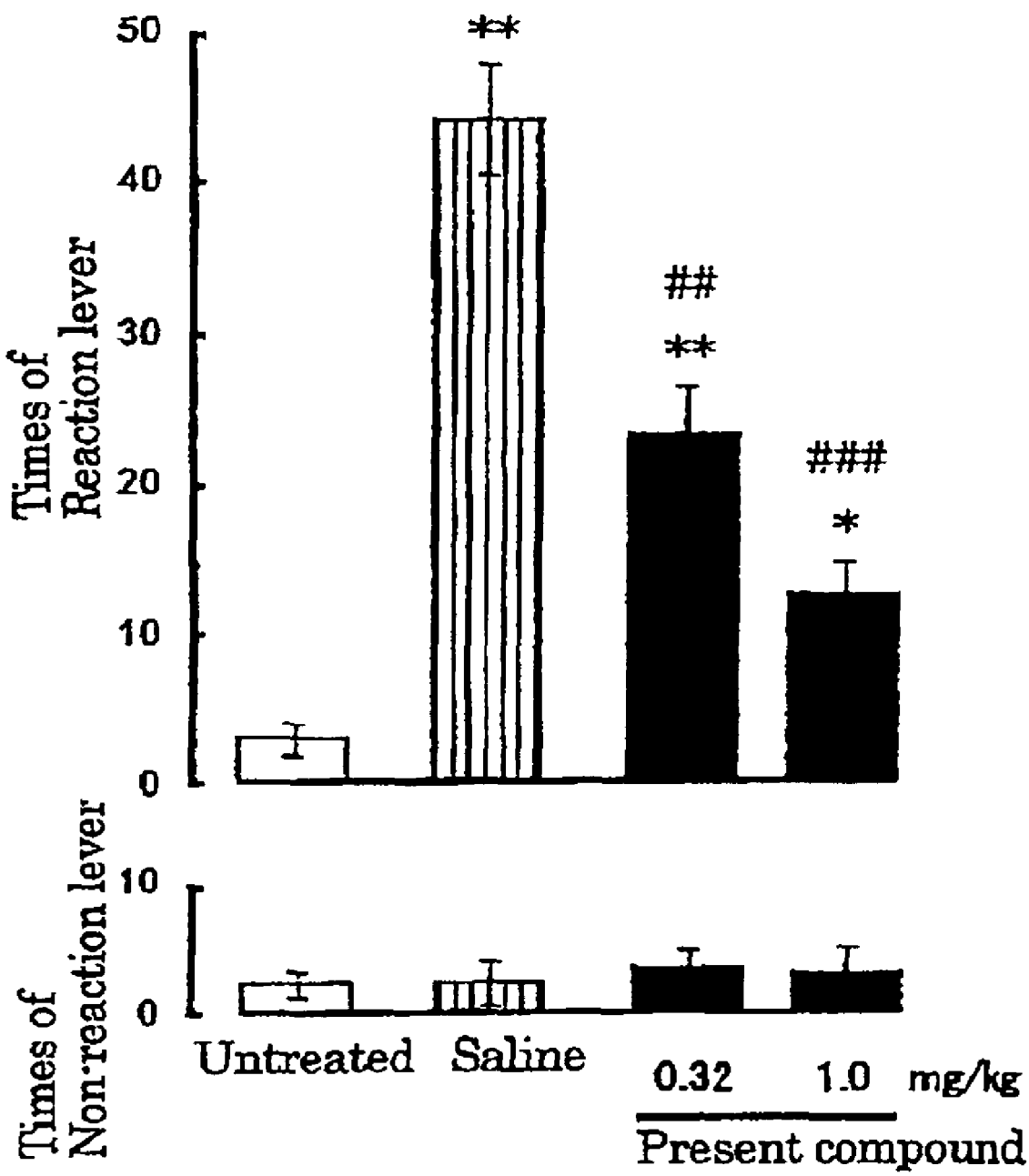
FIG. 2 is a graph showing the inhibitory effect of the compound of the present invention on the substance-seeking behavior by single administration. After single administration of the compound of the present invention (1.0 mg/kg, i.p.), the number of active lever-pressings induced by forced administration of a low dose of methamphetamine, was observed for 30 minutes, and the result is shown in the graph.

Thirty minutes before this stimulation with the drug-associated cue or by the administration of a low dose of methamphetamine, signal administration of the compound of the present invention (0.32, 1.0 mg/kg, i.p.) was carried out, and a change in the methamphetamine-seeking behavior induced by drug-associated cue or by forced administration of methamphetamine was observed. As a result, the seeking behavior was suppressed significantly and dose-dependently (FIGS. 1 and 2).

Figure 3:
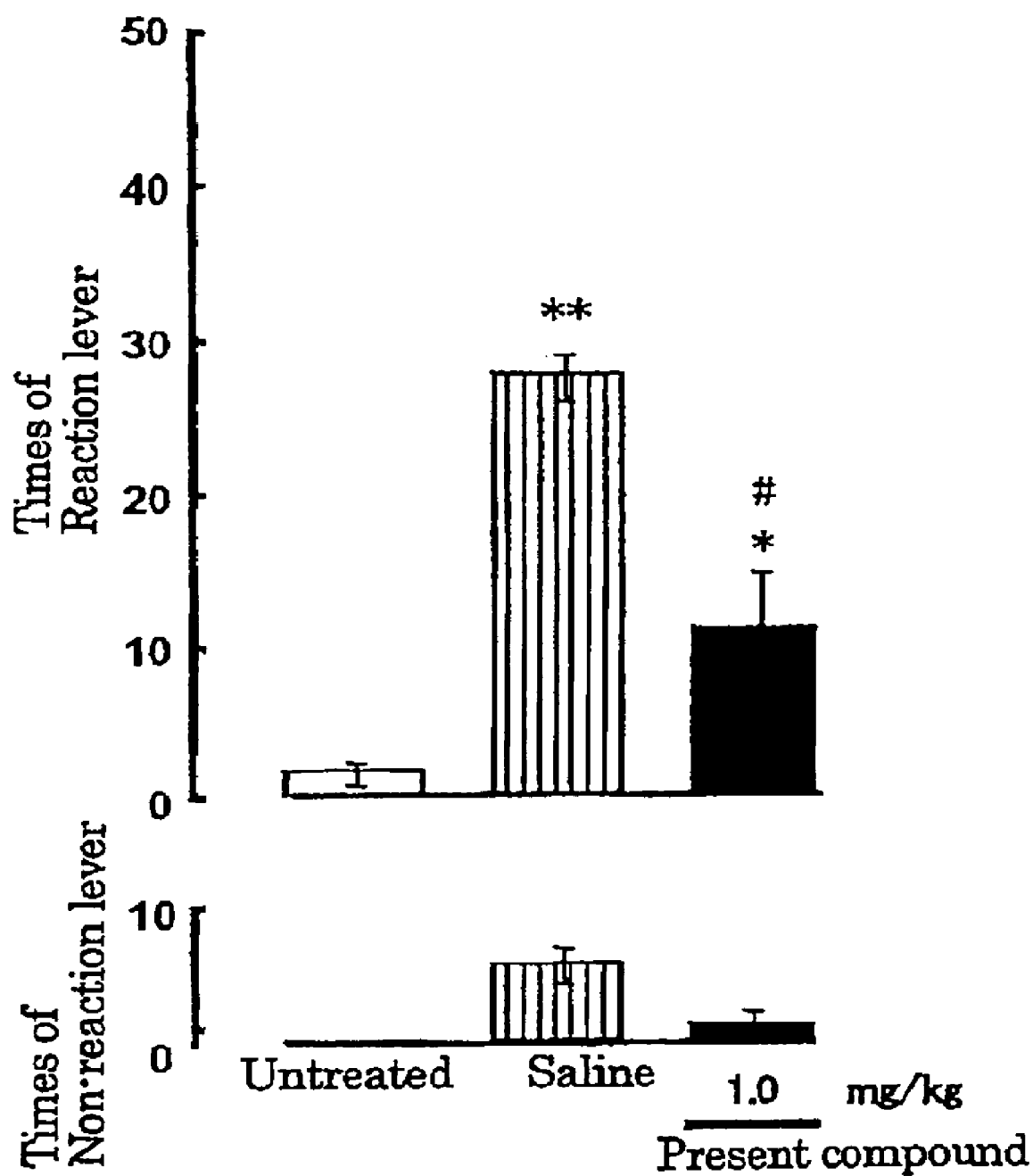
FIG. 3 is a graph showing the inhibitory effect of the compound of the present invention on the substance-seeking behavior by repeated administration. After repeated administration of the compound of the present invention (1.0 mg/kg, i.p.), the number of active lever-pressings induced by drug-associated cue, was observed for 30 minutes, and the result is shown in the graph.
Figure 4:
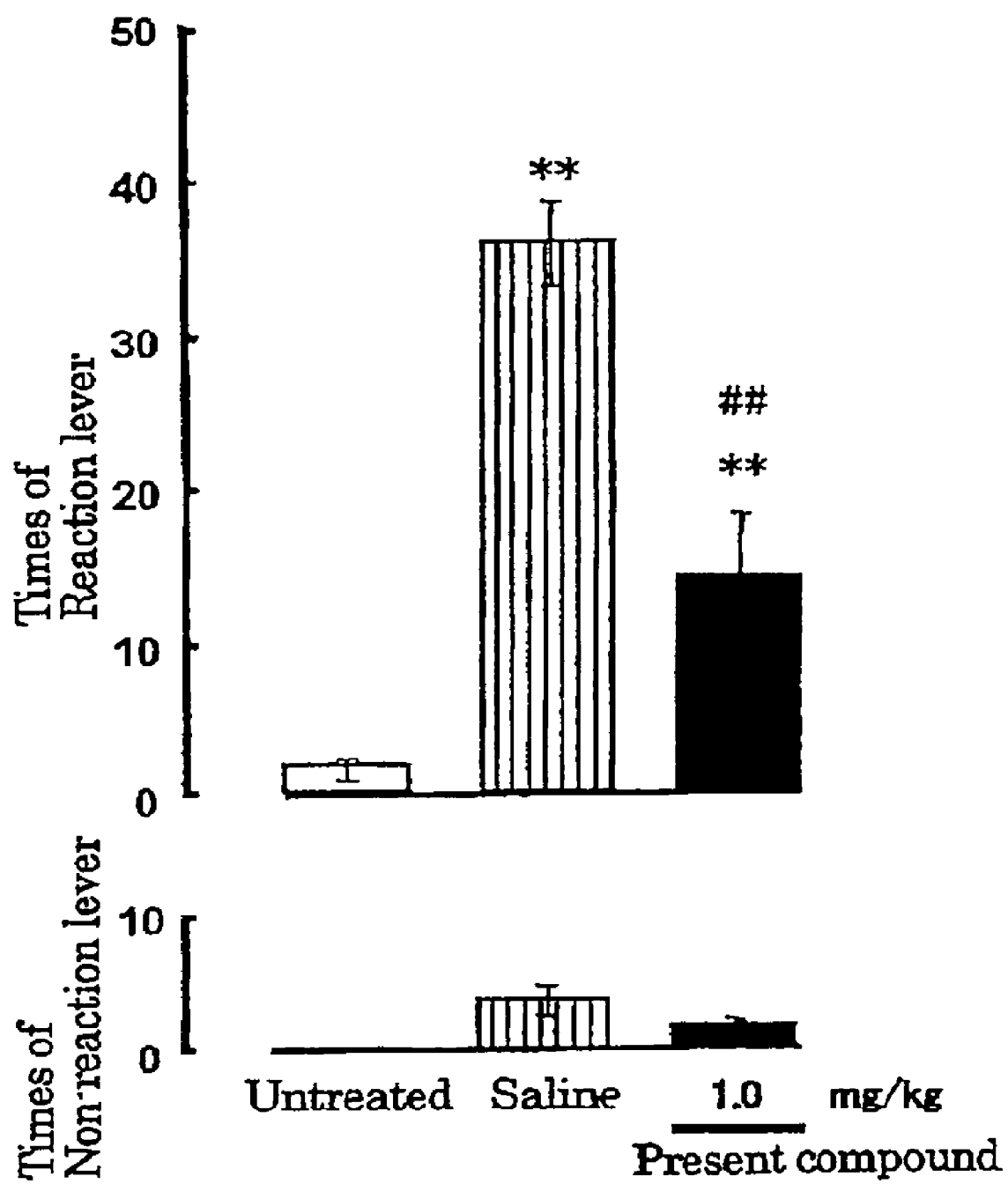
FIG. 4 is a graph showing the inhibitory effect of the compound of the present invention on the substance-seeking behavior by repeated administration. After repeated administration of the compound of the present invention (1.0 mg/kg, i.p.), the number of active lever-pressings induced by forced administration of a low dose of methamphetamine, was observed for 30 minutes, and the result is shown in the graph.

Experiment 2: The Inhibitory Effect of Repeated Administration of the Compound of the Present Invention on Substance-Seeking Behavior In the extinction process for 5 days, the compound of the present invention (1.0 mg/kg, i.p.) was repeatedly administered, and a change in the methamphetamine-seeking behavior induced by drug-associated cue or by forced administration of methamphetamine was observed. As a result, the seeking behavior was suppressed significantly (FIGS. 3 and 4).

Figure 5:
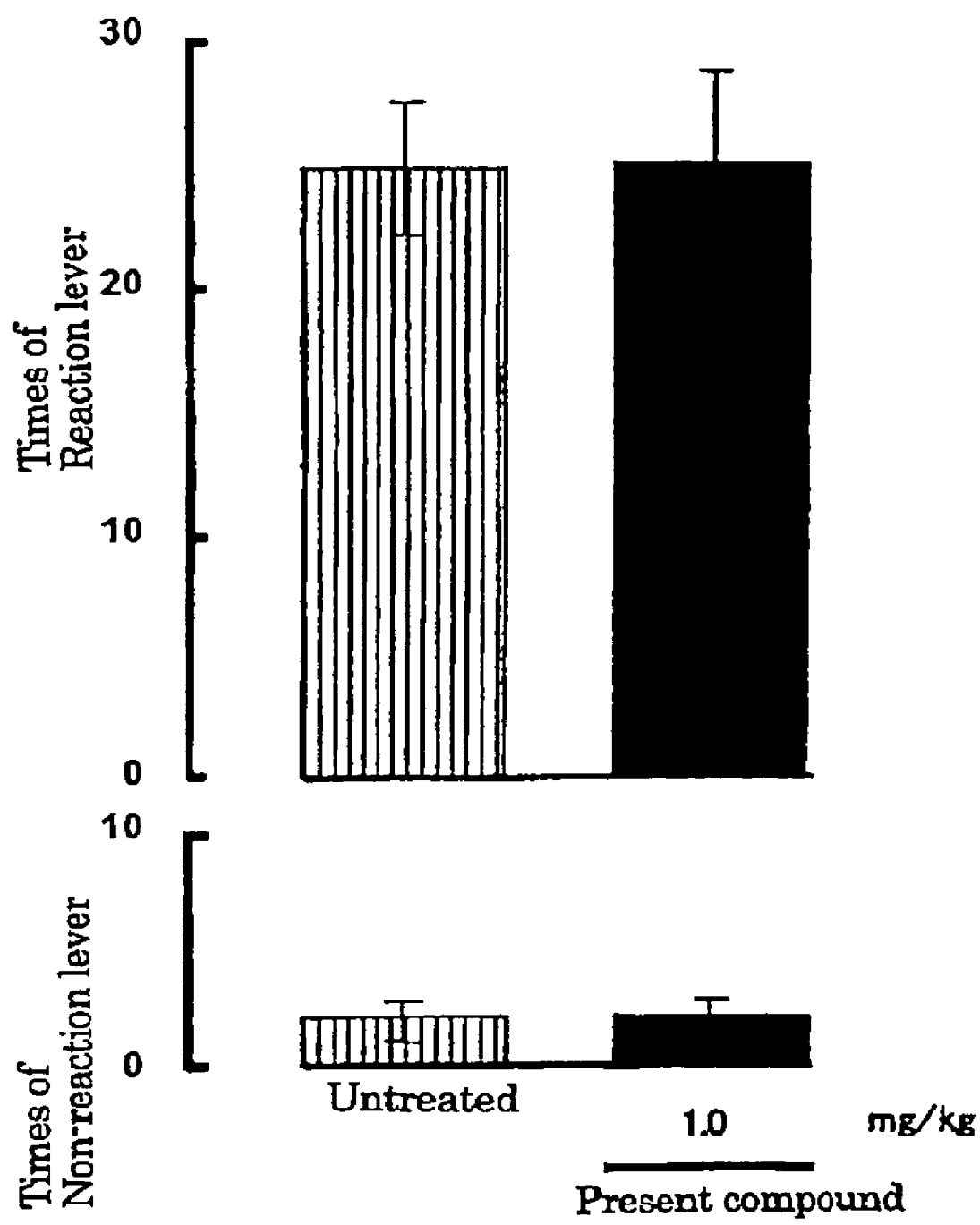
FIG. 5 is a graph showing the influence of the compound of the present invention on methamphetamine self-administration. After administration of the compound of the present invention (1.0 mg/kg, i.p.), the number of active lever-pressings by which methamphetamine was self-administered was observed for 30 minutes, and the result is shown in the graph.

Experiment 3: The Influence of the Compound of the Present Invention on Methamphetamine-Taking Behavior For examining the influence of the compound of the present invention on methamphetamine-taking behavior, 1.0 mg/kg of the compound of the present invention was administered intraperitoneally. As a result, the number of active lever pressings, by which the experimental animal could attain the self-administration (taking) of methamphetamine, was not increased, thus revealing that the compound of the present invention did not exert any influence on the methamphetamine-taking behavior (FIG. 5).

Figure 6:
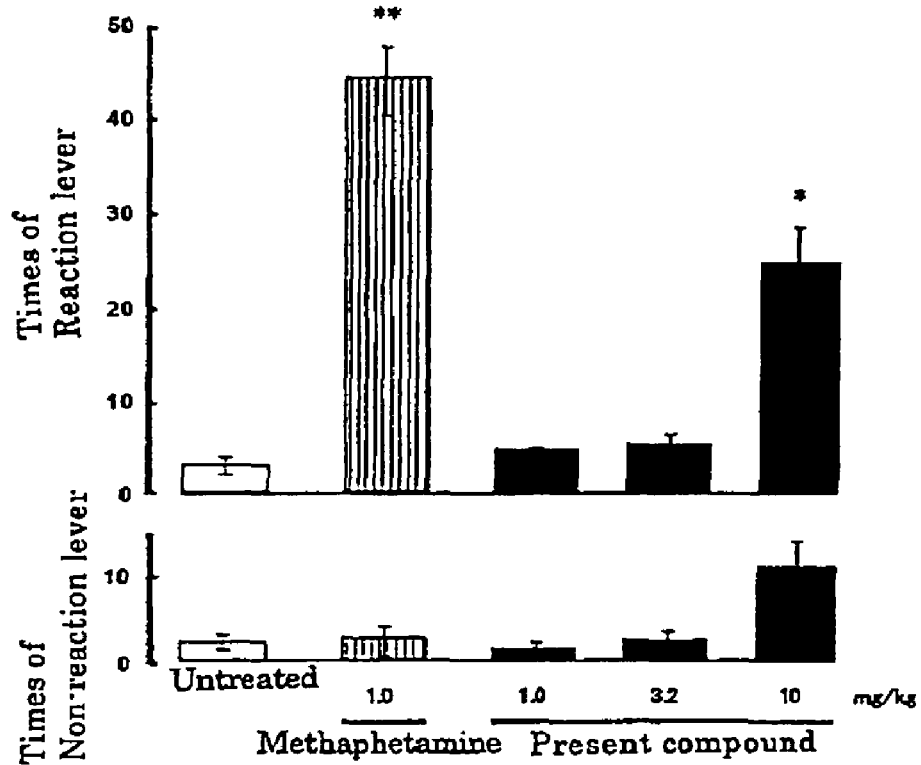
FIG. 6 is a graph showing the influence of the compound of the present invention on occurrence of substance-seeking behavior. The number of active lever-pressings after administration of the compound of the present invention (1.0 mg/kg, 3.2 mg/kg, 10 mg/kg, i.p.) was observed for 30 minutes, and the result is shown in the graph.

Experiment 4: The Influence of the Compound of the Present Invention on Occurrence of Substance-Seeking Behavior For examining the influence of the compound of the present invention on occurrence of substance-seeking behavior, 1.0 mg/kg of the compound of the present invention was administered intraperitoneally. As a result, the methamphetamine seeking behavior was not induced. However, the compound of the present invention at a high dose (10 mg/kg, i.p.), although weak, caused methamphetamine-seeking behavior (FIG. 6).

Experiment 5: The Inhibitory Effect by Single Administration of the Compound of the Present Invention on Substance-Seeking Behavior with Coadministration of a Dopamine D1 or D2 Receptor Antagonist On day 6 of the extinction process, substance-seeking behavior ("craving") was induced by drug-associated cue (tone and light) or by administering a low dose of methamphetamine (1.0 mg/kg, intraperitoneal (i.p.) administration).

Figure 7:
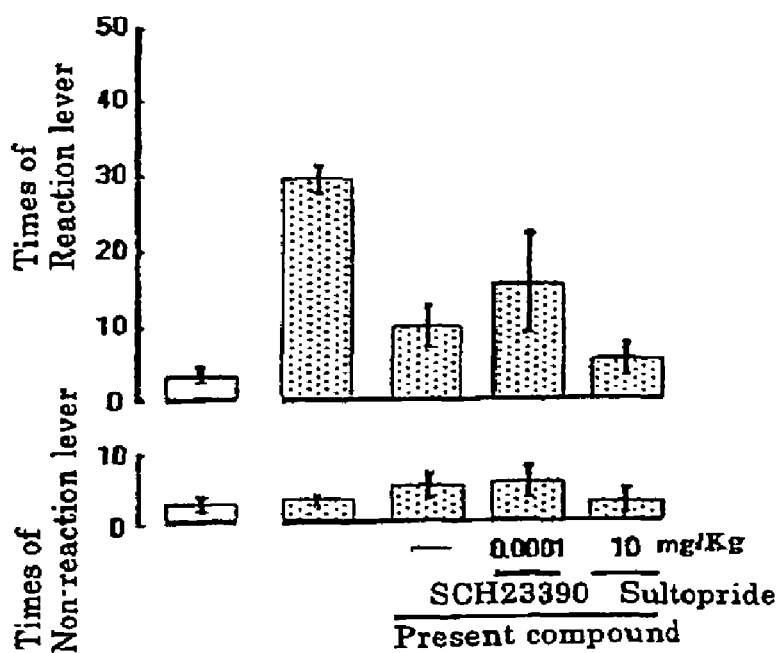
FIG. 7 is a graph showing the effect of the compound of the present invention in the coexistence of a dopamine D1 or D2 receptor antagonist. After single administration of the compound of the present invention (1.0 mg/kg, i.p.), dopamine D1 receptor antagonist SCH23390, (R-(+)-7-chloro-8-hydroxy-3-methyl-1-phenyl-2,3,4,5-tetrahydro-1H-3-benza zepine hydrochloride) (0.0001 mg/kg, s.c.) or a D2 receptor antagonist sultopride, the number of active lever-pressings induced by drug-associated cue, was observed for 30 minutes, and the result is shown in the graph.
Figure 8:
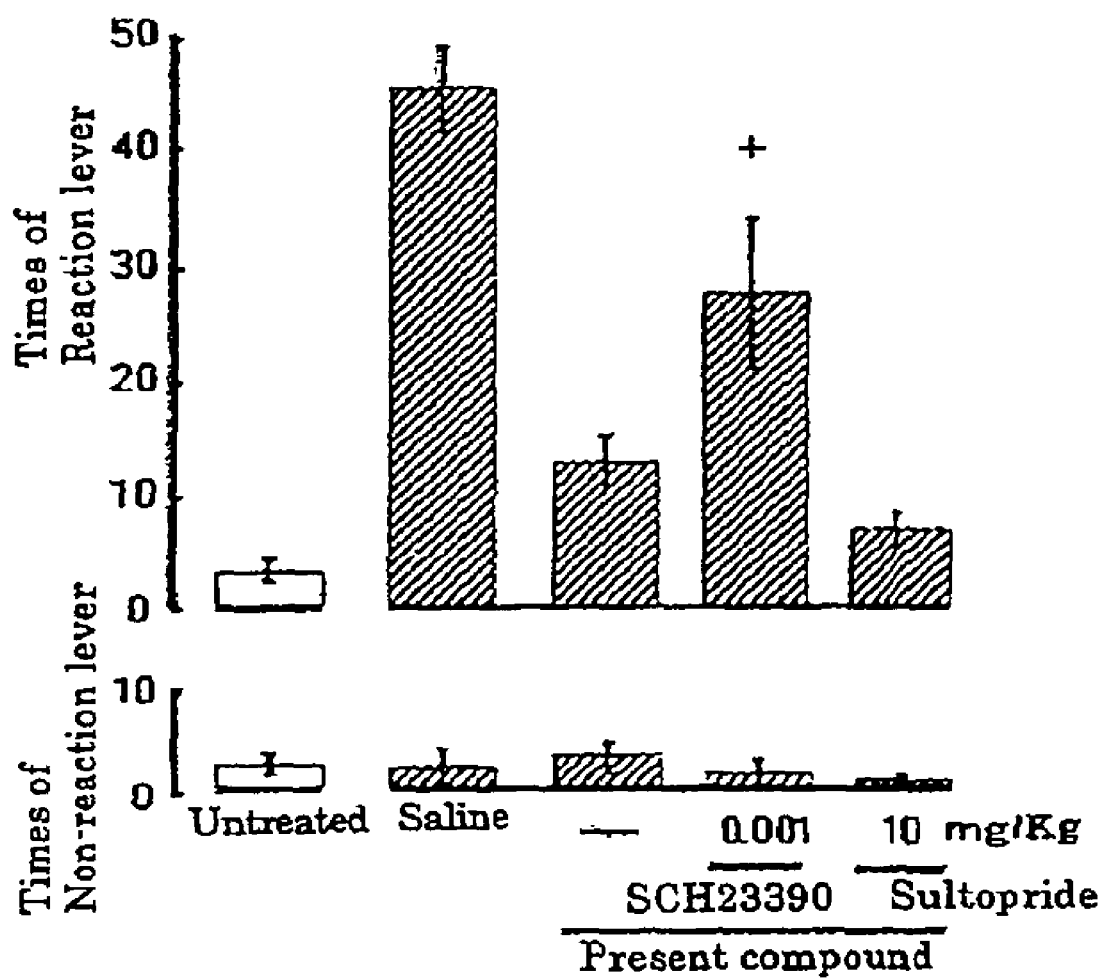
FIG. 8 is a graph showing the effect of the compound of the present invention in the coexistence of a dopamine D1 or D2 receptor antagonist. After single administration of the compound of the present invention (1.0 mg/kg, i.p.) and a dopamine D1 receptor antagonist SCH23390, (R-(+)-7-chloro-8-hydroxy-3-methyl-1-phenyl-2,3,4,5-tetrahydro-1H-3-benza zepine hydrochloride) (0.0001 mg/kg, s.c.) or a D2 receptor antagonist sultopride, the number of active lerver-pressings induced by forced administration of a low dose of methamphetamine, was observed for 30 minutes, and the result is shown in the graph. The symbol + indicates statistical significance +: $p<0.05$ vs. a treated group with 1.0 mg/kg of the compound of the present invention.

Thirty minutes before drug-associated cue or by the administration of a low dose of methamphetamine, the compound of the present invention (0.32, 1.0 mg/kg, i.p.) and a dopamine D1 receptor antagonist SCH23390, (R-(+)-7-chloro-8-hydroxy-3-methyl-1-phenyl-2,3,4,5-tetrahydro-1H-3-benza zepin hydrochloride) (0.0001 mg/kg, s.c.) or a D2 receptor antagonist sultopride were administered. The methamphetamine-seeking behavior induced by drug-associated cue showed a tendency to be antagonized by the dopamine D1 receptor antagonist SCH23390 (0.0001 mg/kg, s.c.), but not by the dopamine D2 receptor antagonist sultopride (10 mg/kg, i.p.) (FIG. 7). The methamphetamine-seeking behavior induced by administering a low dose of methamphetamine was antagonized by the dopamine D1 receptor antagonist SCH23390 (0.001 mg/kg, s.c.), but not by the dopamine D2 receptor antagonist sultopride (10 mg/kg, i.p.) (FIG. 8).

As is evident from the experiments shown above, the frequency of lever-pressings was significantly increased by drug-associated cue or by forced administration of methamphetamine, and the methamphetamine-seeking behavior was recognized. This methamphetamine-seeking behavior was significantly suppressed by repeated administration in the extinction process for 5 days or even by single administration 30 minutes before measurement of methamphetamine-seeking behavior. The compound of the present invention at a dose that suppressed the methamphetamine-seeking behavior did not induce the methamphetamine-seeking behavior. It is suggested that the effect of the compound of the present invention is attributable to the inactivation of dopamine D1 receptor.

The invention claimed is:

1. A method of treating substance dependence, which comprises administering an effective amount of (−)-1-(benzofuran-2-yl)-2propylaminopentane, or a pharmaceutically acceptable salt thereof, to a substance-dependent patient, wherein the substance is a member selected from the group consisting of methamphetamine, amphetamine, 3,4-methylenedioxy-N-methylamphetamine (MDMA) and cocaine.

2. A method of suppressing the induction of substance-seeking behavior, which comprises administering an effective amount of (−)-1-(benzofuran-2-yl)-2-propylaminopentane, or a pharmaceutically acceptable salt thereof, to a substance-dependent patient with substance-seeking behavior, wherein the substance is a member selected from the group consisting of methamphetamine, amphetamine, 3,4-methylenedioxy-N-methylamphetamine (MDMA) and cocaine.

3. The method of treating substance dependence according to claim 1, wherein the substance is a member selected from the group consisting of methamphetamine, amphetamine and cocaine.

4. The method of suppressing the induction of substance-seeking behavior according to claim 2, wherein the substance is a member selected from the group consisting of methamphetamine, amphetamine and cocaine.

* * * * *